United States Patent [19]
Mueller et al.

[11] Patent Number: 6,019,756
[45] Date of Patent: Feb. 1, 2000

[54] LASER DEVICE FOR TRANSMYOCARDIAL REVASCULARIZATION PROCEDURES

[75] Inventors: Richard L. Mueller, Byron; Stuart D. Harman, San Jose; Richard D. Phipps, Morgan Hill, all of Calif.

[73] Assignee: Eclipse Surgical Technologies, Inc., Sunnyvale, Calif.

[21] Appl. No.: 08/790,193

[22] Filed: Jan. 30, 1997

Related U.S. Application Data

[63] Continuation-in-part of application No. 08/628,849, Apr. 5, 1996, Pat. No. 5,738,680, and a continuation-in-part of application No. 08/628,456, Apr. 5, 1996, Pat. No. 5,782,823.

[51] Int. Cl.$^7$ .................................................. A61B 17/36
[52] U.S. Cl. ................................... 606/7; 606/15
[58] Field of Search ..................... 606/7, 13–16, 606/11, 10, 167, 170; 607/89

[56] References Cited

U.S. PATENT DOCUMENTS 4,846,171  7/1989  Kauphusman et al. .................... 606/16

FOREIGN PATENT DOCUMENTS

| | | |
|---|---|---|
| 0515867 A2 | 2/1992 | European Pat. Off. . |
| WO 94/14383 A1 | 7/1994 | WIPO . |
| WO 95/17127 A1 | 6/1995 | WIPO . |
| WO 96/39964 A1 | 6/1996 | WIPO . |

Primary Examiner—Ruth S. Smith
Attorney, Agent, or Firm—Ray K. Shahani; Janet Kaiser Castaneda

[57] ABSTRACT

A laser surgery device for performing laser myocardial revascularization procedures on a human heart comprises a hand-held body portion with a forwardly extending probe member with an enlarged head end assembly including a piercing tip. A movable fiber bundle connected to a laser source extends through the body portion and the probe member with its distal tip at the head end assembly. A control button on the body portion enables the device to move the distal tip forwardly from the head end, and selectable stop members are provided on the body portion to provide different travel distances for the optical fiber bundle during a procedure. The body portion has a rotatable nosepiece with an internal ratchet mechanism which enables the device user to rotate the probe member and its head end to a selected optimum position before commencing a procedure. The head end assembly includes an easily replaceable piercing member in combination with a concave disk having a yieldable liner for cushioning the head assembly contact with the patient's heart. The device is used with a TMR procedure wherein the epicardium is initially pierced to provide access to the myocardium for the distal tip of the fiber bundle which then emits laser pulses as it is moved through the myocardium.

24 Claims, 11 Drawing Sheets

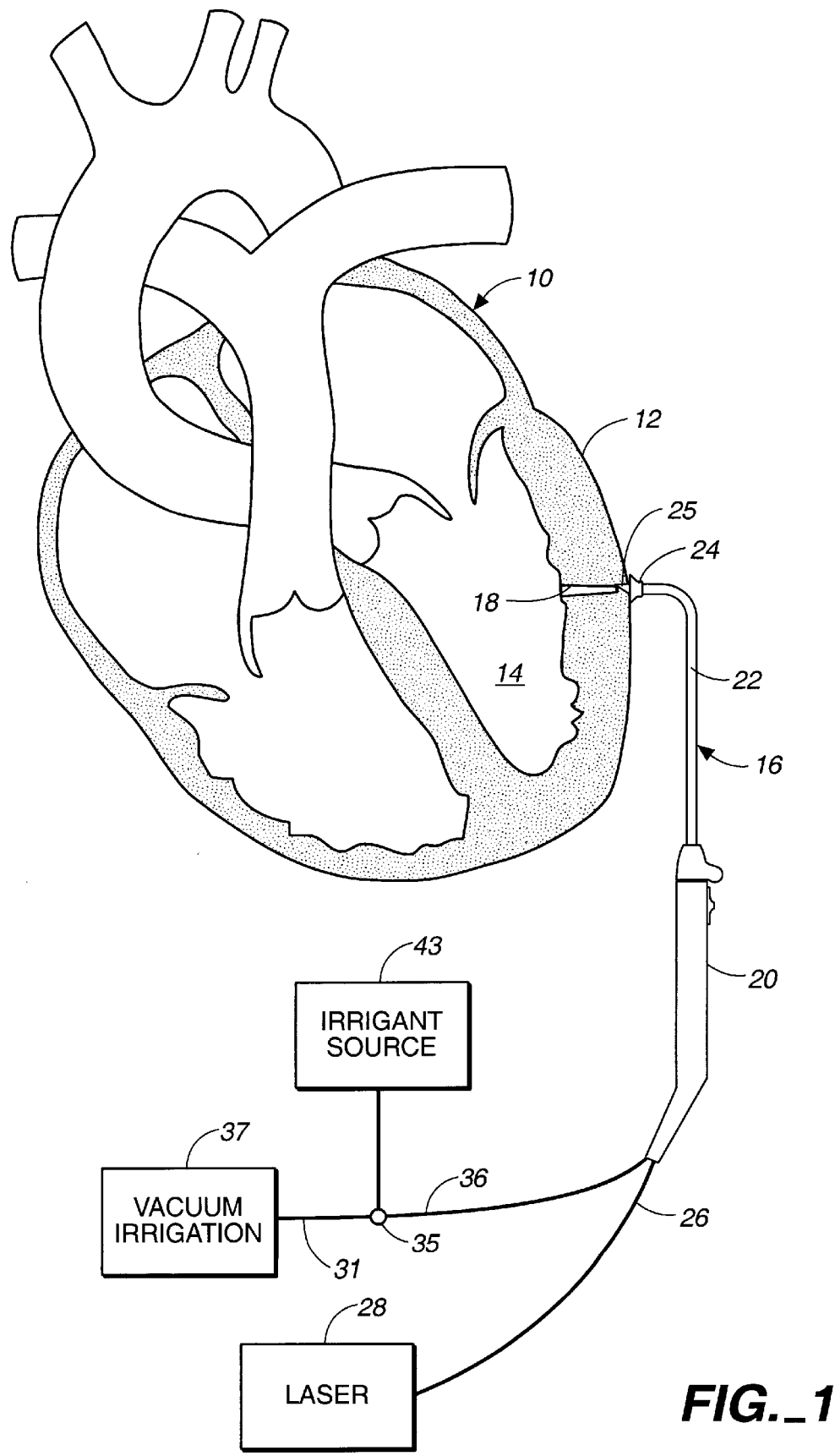
FIG._1

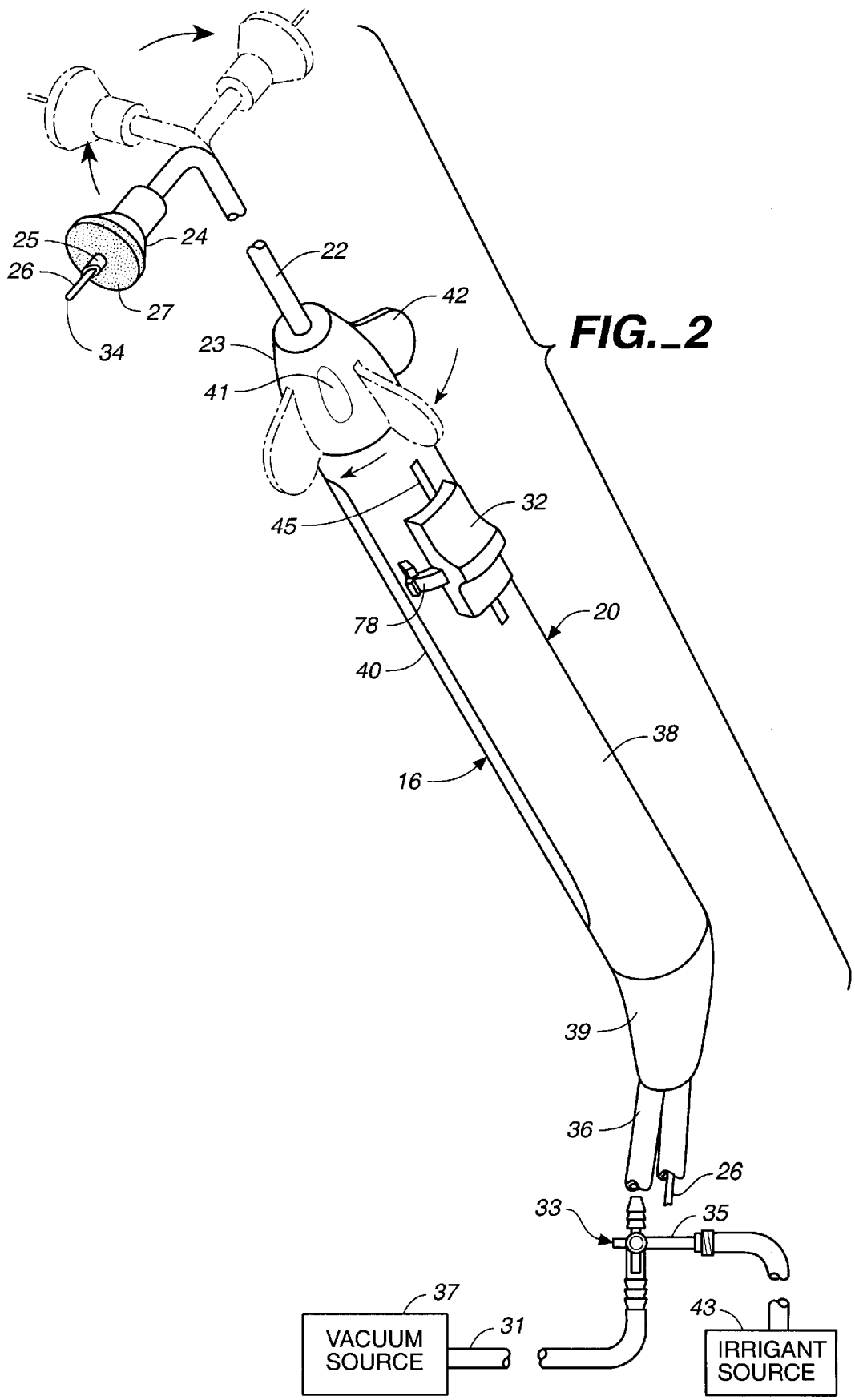
FIG._2

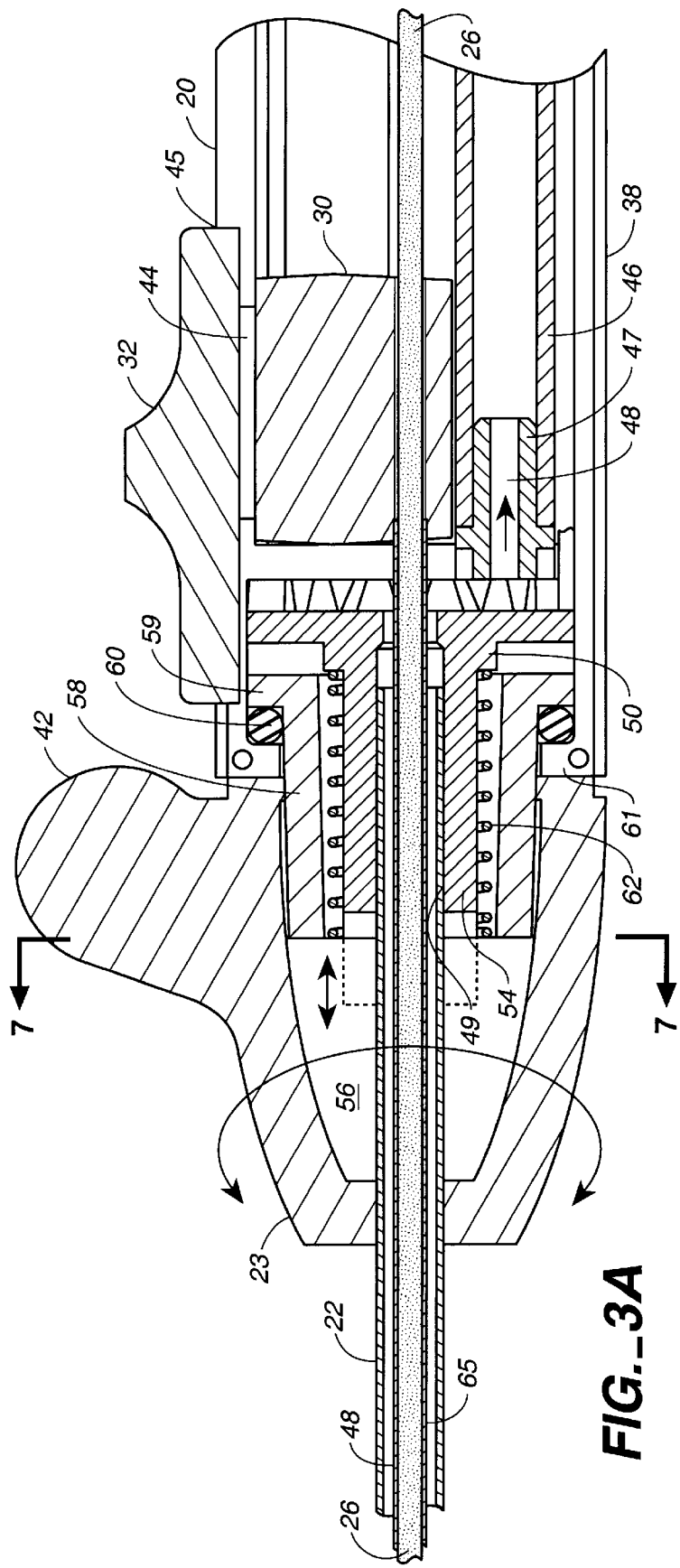
FIG._3A

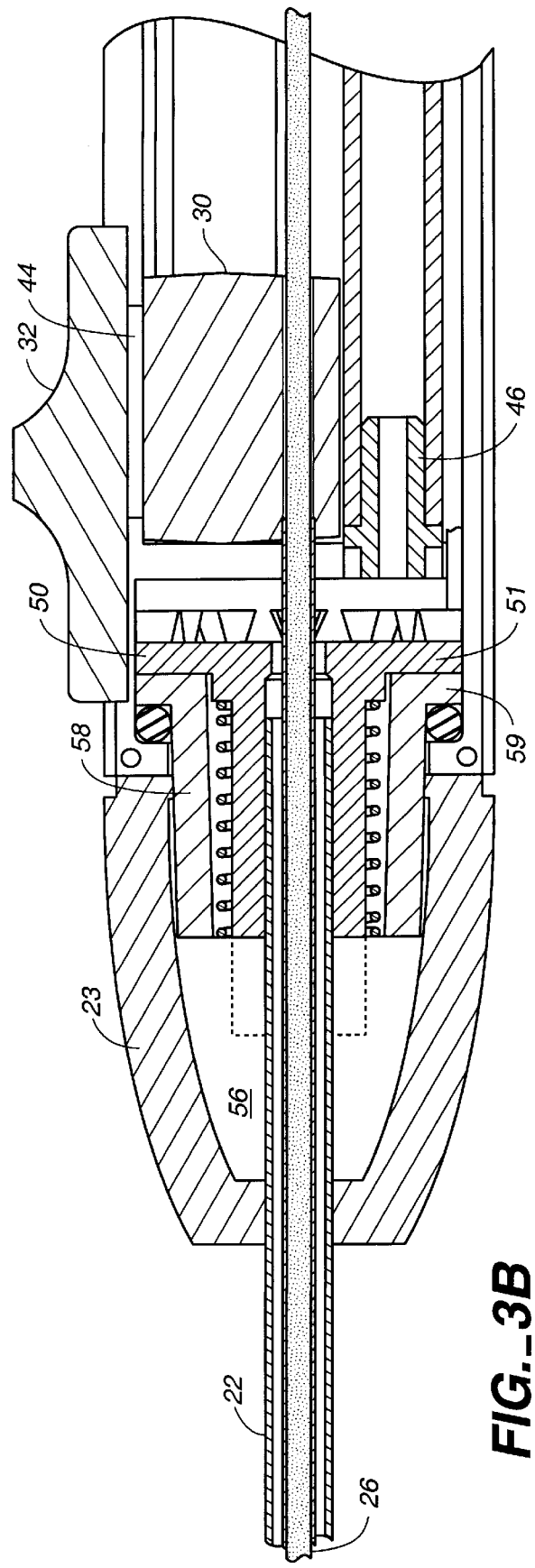
FIG._3B

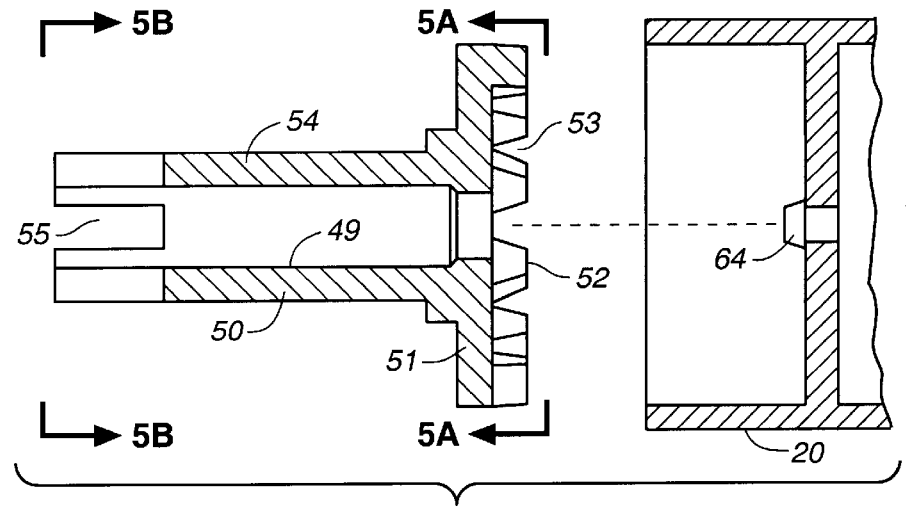
FIG._4
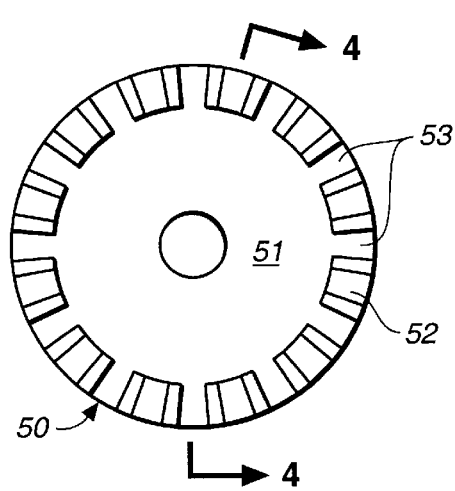
FIG._5A
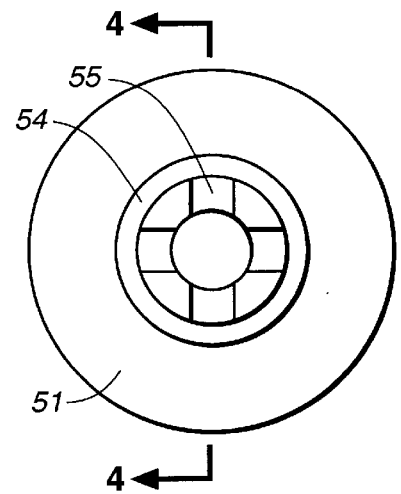
FIG._5B
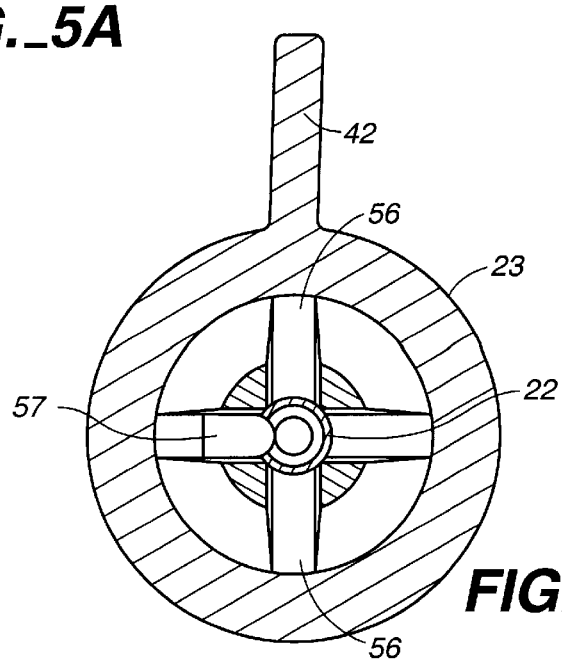
FIG._7

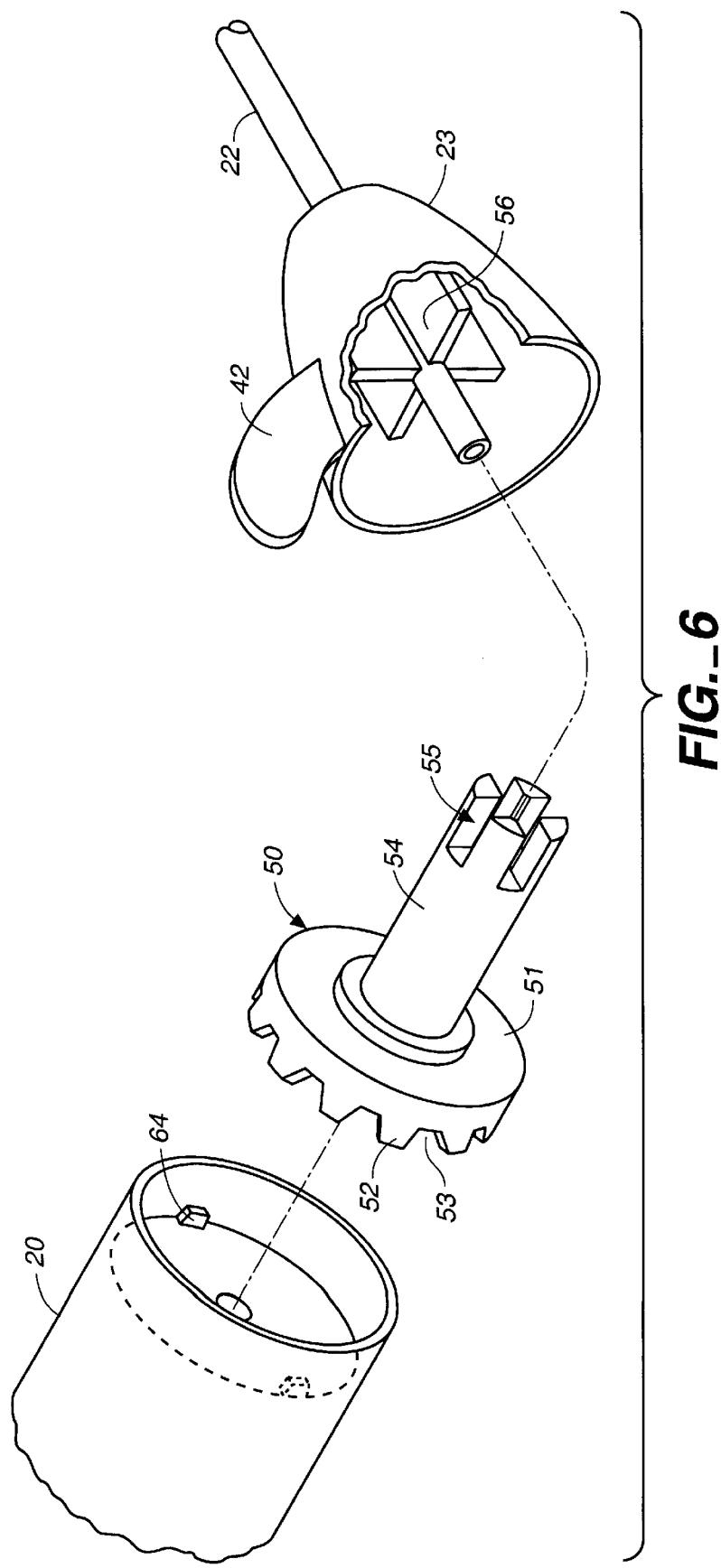
FIG._6

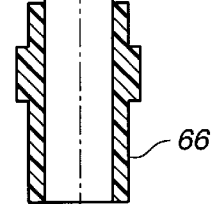
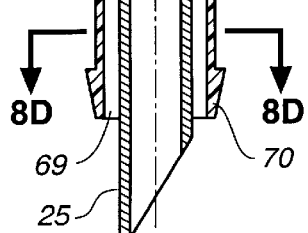
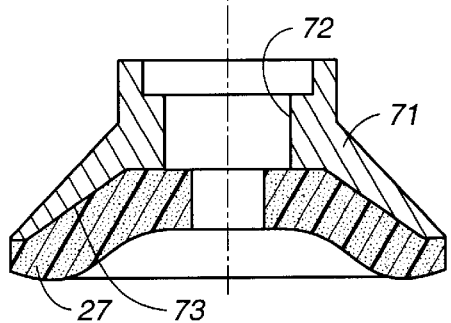
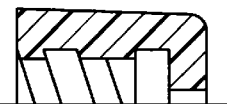
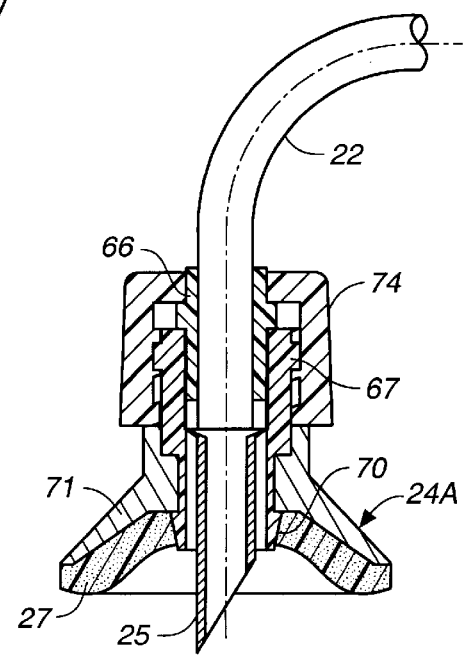
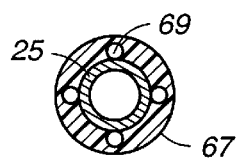
FIG._8
FIG._8A
FIG._8D

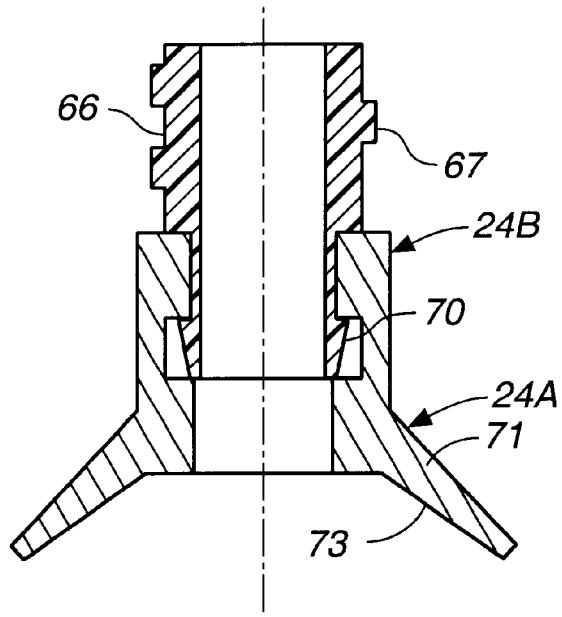
FIG._8B
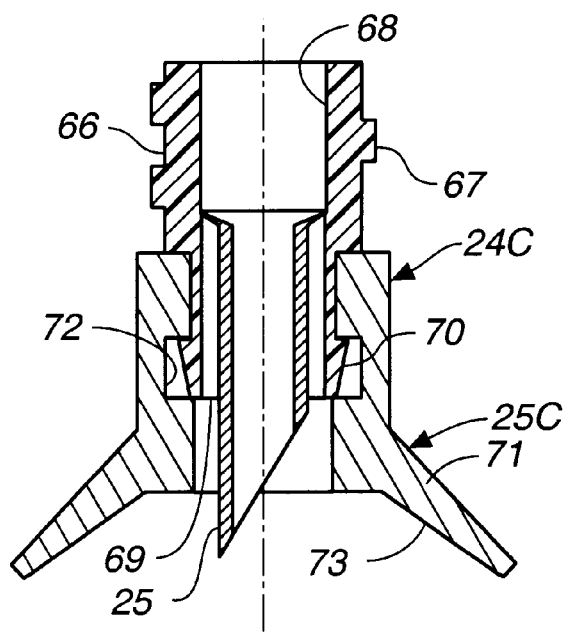
FIG._8C

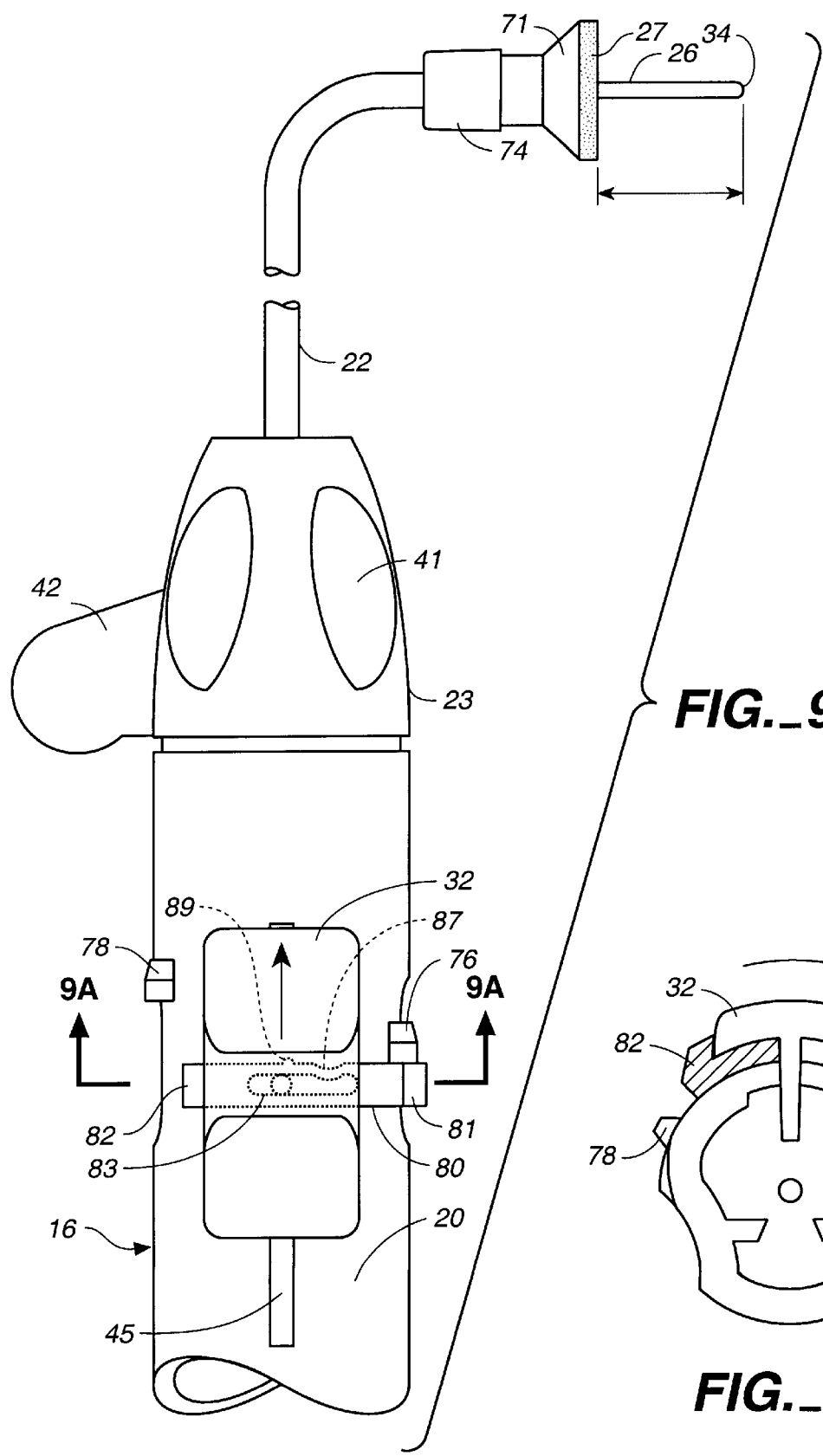
FIG._9
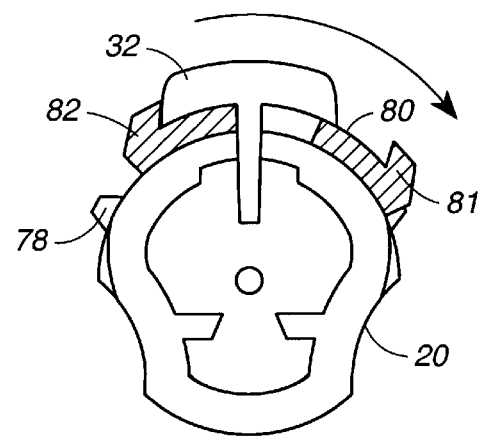
FIG._9A

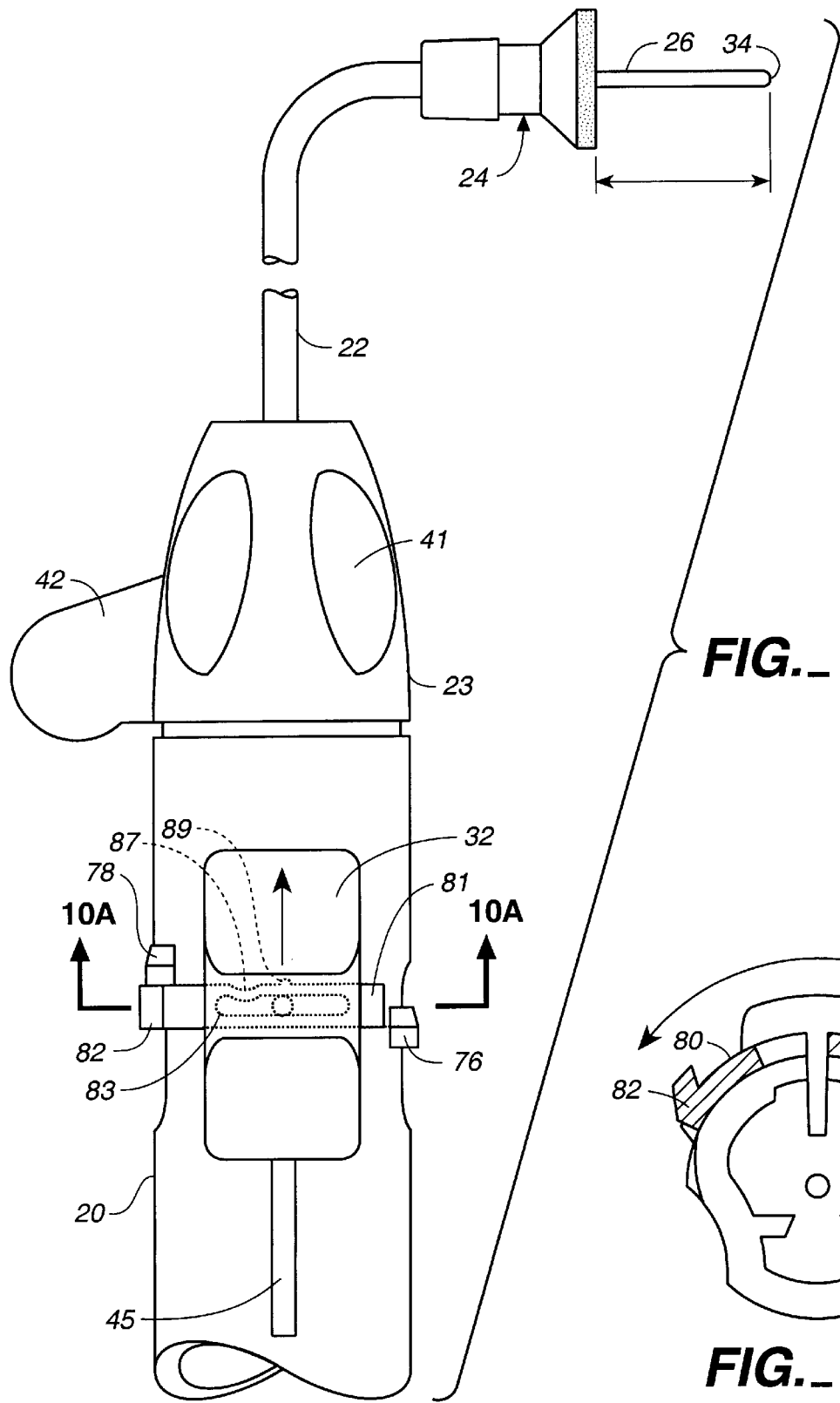
FIG._10
FIG._10A

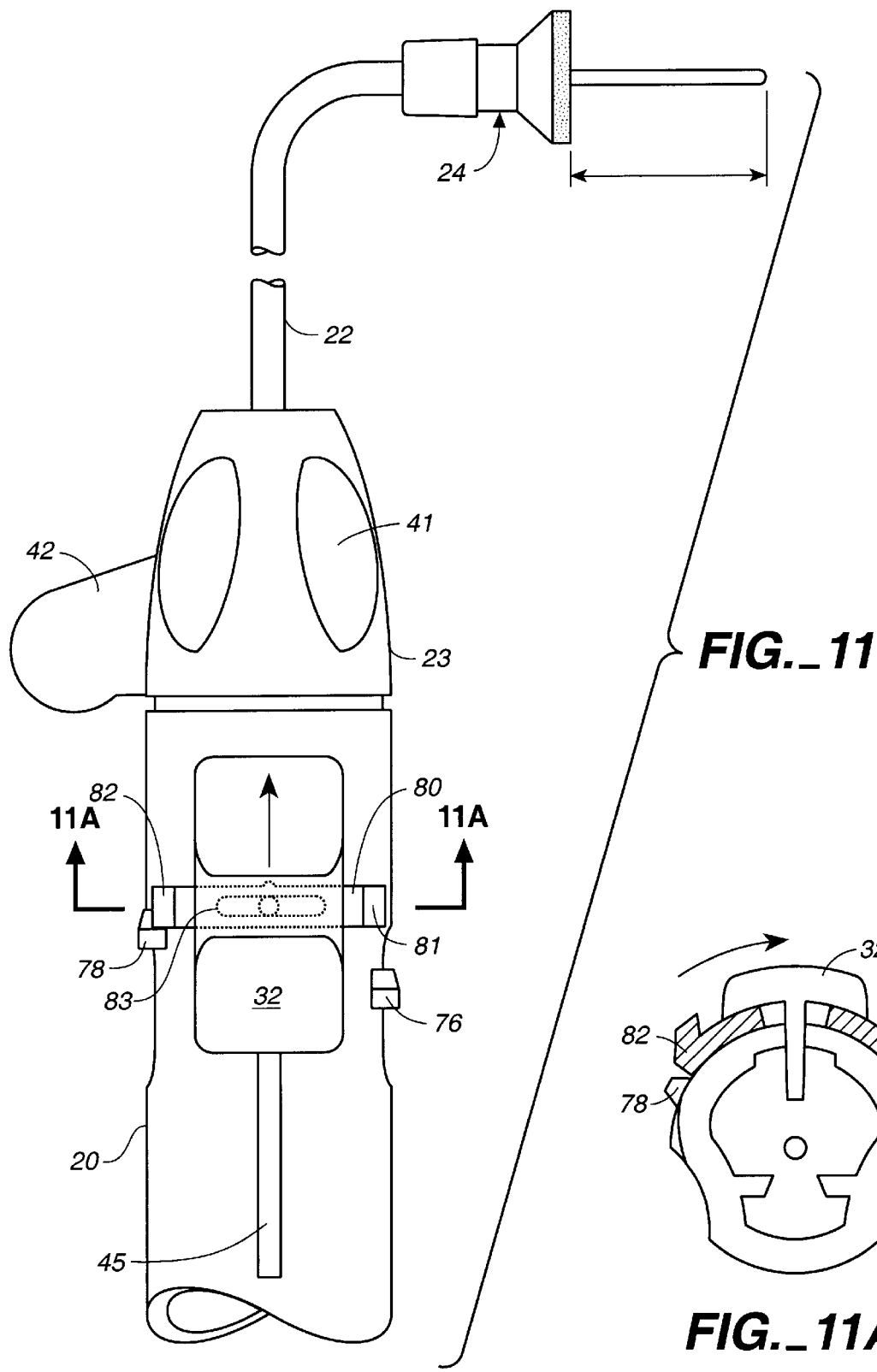

LASER DEVICE FOR TRANSMYOCARDIAL REVASCULARIZATION PROCEDURES

RELATED APPLICATIONS

This application is a continuation-in-part of U.S. patent application Ser. No. 08/628,849, filed on Apr. 5, 1996, now U.S. Pat. No. 5,738,680 incorporated herein by reference, and U.S. patent application Ser. No. 08/628,456, filed on Apr. 5, 1996, now U.S. Pat. No. 5,782,823 incorporated herein by reference.

FIELD OF INVENTION

This invention relates to the field of laser surgery, and more particularly to an improved laser surgery device for use in procedures for increasing the flow of blood to heart muscle.

BACKGROUND OF THE INVENTION

Medical science has developed a wide variety of methods for counteracting the effects of cardiovascular disease including open heart and by-pass surgery. Non-surgical procedures such as percutaneous transluminal coronary angioplasty, laser angioplasty, and atherectomy have also been developed.

One alternative to the aforementioned procedures is known as Transmyocardial Revascularization (TMR). In such procedures, channels are formed in the ventricle wall of the heart with a laser. These channels provide blood flow to ischemic heart muscle. A history and description of this method has been documented by Dr. M. Mirhoseini and M. Cayton on "Lasers in Cardiothoracic Surgery" in Lasers in General Surgery (Williams & Wilkins; 1989) pp. 216–233.

As described therein, a CO2 laser was used to produce channels in the ventricle from the epicardium through the myocardium. This procedure followed a surgical incision in the chest wall to expose the heart. Laser energy was transmitted from the laser to the epicardium by means of an articulated arm device of the type commonly used for CO2 laser surgery. The beam was coherent and traveled as a collimated beam of laser energy through the epicardium, the myocardium and the endocardium into the left ventricle cavity. The epicardium received the highest energy density and therefore normally had the largest area of heart tissue removed compared with the endocardium which was approximately 1 cm deep to the epicardium. The resultant channel through the myocardium was funnel-like, with the greatest channel diameter located at the epicardium. A problem associated with the above procedure arose because laser perforation of the epicardium caused bleeding from it outwardly from the left ventricle after the procedure. External pressure by the surgeon's hand on the epicardium of the heart was often needed to stop bleeding from the ventricle to the outside through the hole produced by the laser in the epicardium. However, this procedure was usually only partially successful because it resulted in a significant amount of blood loss and/or an excessive amount of time required to stop the bleeding. Both factors could jeopardize the success of the revascularization procedure.

In a proposed improvement in an TMR procedure described in Hardy U.S. Pat. No. 4,658,817, a needle was added to the distal tip of an articulated arm system, with a beam of laser energy being passed through the lumen of the needle. The metal tip of the needle of the device was used to pierce most of the myocardium and the laser beam then was used to create the desired channel through the remaining portion of the myocardium and through the adjacent endocardium. In the Hardy procedure, the hollow needle used to deliver laser light was subject to being clogged by tissue or blood which could flow into the needle, thus blocking the laser light from impinging the myocardium. Also, the metal rim of the needle could be damaged by the intense $CO_2$ laser light and leave contaminating metal remains within the myocardium which are potentially hazardous.

Another proposed TMR procedure is described in the Aita, et al U.S. Pat. No. 5,380,316. Aita, commenting on the Hardy needle device, contends that mechanical piercing was undesirable because it entailed some degree of tearing of the pierced tissue, and that tearing often leads to fibrosis as the mechanical tear heals, a factor said by Aita to severely diminish the effectiveness of the LMR treatment. Aita, et al also contends that exposure to metal may cause fibrosis where the needle passes through tissue. The Aita, et al patent describes an elongated flexible lasing apparatus which is guided to an area exterior to the patient's heart and irradiates the exterior surface to form a channel through the epicardium, myocardium and endocardium. Thus, in the Aita et al procedure, the epicardium is irradiated at a high energy density and therefore should have a large area of heart tissue removed. Consequently, the Aita, et al procedure has the same problems and disadvantages as the prior Mirhoseini TMR procedure with respect to the aforementioned bleeding problem in the outer surface of the epicardium.

In U.S. Pat. No. 5,713,894 which is assigned to the assignee of the present application, an improved apparatus and method for TMR procedures is disclosed. In this application the epicardium membrane of the heart muscle is first penetrated mechanically by a hollow piecing member and thereafter the distal end of a laser transmitting fiber is moved forwardly through the myocardium as it emits pulses of laser energy to form a channel. When the fiber element is retracted and the piercing member is removed, the opening that was made mechanically in the epicardium tends to close to prevent excessive bleeding from the channel formed in the myocardium. In the above copending application a laser surgery device is disclosed for performing TMR procedures in the aforesaid manner. The present invention provides a further improved laser surgery device for performing similar TMR procedures with unique and advantageous features.

SUMMARY AND OBJECTS OF THE INVENTION

To carry out a complete TMR procedure according to a desired method, it is generally necessary to form a number of closely spaced apart perforations in the side wall of the patient's heart. For each perforation, the surgeon must place the end of the operating instrument (the laser surgery device) against the surface of the beating heart and hold it in position as the laser emitting fiber element is moved forward to form an angiogenesis pocket in the myocardium or a channel through the myocardium into the left ventricle chamber. Often it is necessary for the surgeon to manipulate the operating instrument in such a manner so as to gain access to an outer surface area of the heart that normally might be difficult to reach. Thus, it is highly desirable that the operating instrument be one which is relatively light, easy to maneuver and manipulate as well as one which will perform its desired laser pulsing function with precision and with a short cycle time. A general object of the invention is to provide an improved operating instrument for TMR procedures that solves these problems.

Another object of the invention is to provide an operating instrument for TMR procedures having a tubular J-shaped probe member extending from a main body that forms a handle held by the surgeon and with means for rotating the probe member so that its distal end can be easily manipulated and thereby placed in a desired target area on the surface of the patient's heart.

Another object of the invention is to provide an operating instrument for use in TMR procedures having a main hand held body and means thereon for controlling the axial distance of travel for an optical fiber element that extends through the body during a typical TMR procedure.

Another object of the invention is to provide a laser surgery device having means for selecting different limits of travel for an optical fiber element during TMR procedure.

A further object of the invention is to provide an improved operating instrument for performing TMR procedures which is light and easy to manipulate and yet reliable, durable and precise in its operation.

Still another object of the invention is to provide a device for use in a TMR procedure which uses a concave distal end member with a soft, yieldable lining that contacts and conforms to the outer surface of the epicardium as the heart is beating so that the end member will remain in close contact with the epicardium surface as the optical fiber bundle moves through the distal end member during a TMR procedure.

Yet another object of the invention is to provide an operating instrument for performing TMR procedures having a fluid passage from its proximal to its distal tip so that either a suction force or an irrigating fluid can be selectively applied to the patient's heart during a TMR procedure.

The present invention comprises a hand-held laser surgery device particularly adapted for myocardial revascularization of a human heart that fulfills the aforesaid objectives. The device comprises a body portion shaped so that it can be easily gripped by the surgeon and having a forwardly extending shaped probe member. An integrated optical fiber assembly attached to a laser power source extends through the body portion and the probe member to a distal head assembly on its distal end. The latter includes a disk having a bore through which the distal tip of the fiber bundle can pass. An optional yieldable sponge-like lining is provided on the inner surface of the disk and surrounds a tubular piercing member through which the optical fiber extends. At the forward end of the body portion is a rotatable nose portion which is fixed to the shaped probe member. This nose portion has an external fin which can be engaged by the surgeon's finger to cause rotation of the nose portion and the probe member. This enables the surgeon to orient the distal end of the probe member in the most advantageous position thereby enabling him to reach desired areas on the surface of the patient's heart quickly and efficiently.

On the outside of the body is a sliding control button for moving the fiber bundle axially back and forth. The control button is operatively connected to the fiber within the body and is movable within a slot in the top surface of the body. The axial travel of the control button and thus the fiber bundle can be limited to one or more selectable distances.

Within the body the optical fiber assembly is supported so that it cannot buckle and its movement will be free from or with only minimal friction. During a typical TMR procedure the surgeon can manipulate the device to the desired location and cause the distal end disk on the probe to contact the outer surface of the patient's heart. As this is done, the piercing member at the distal end of the probe position pierces the epicardium and anchors the device thereto. The surgeon can then move the control button forward and thus cause the distal tip of the fiber element to move through the myocardium. As this is done, an air suction or irrigation conduit connected through the body to the distal head end assembly can be selectively applied to provide a means for stabilizing the tip onto the heart surface and for keeping the outer surface of the epicardium firmly against the disk of the distal end assembly or for maintaining a moist TMR site on the heart surface respectively. Sealing of the epicardium occurs after the fiber bundle is withdrawn, the vacuum is discontinued to release the epicardium within the concave distal end member, and the device is moved. Because the preliminary pierced opening in the epicardium substantially closes at this point, a minimum of bleeding occurs after each TMR procedure.

Other objects, advantages and features of the present invention will be apparent to those skilled in the art from the following detailed description and the accompanying drawings.

BRIEF DESCRIPTION OF DRAWINGS

FIG. 1 is a schematic view in section of a human heart showing revascularization of the myocardium utilizing a device according to the present invention.

FIG. 2 is an enlarged view in perspective showing a device embodying principles of the invention for implementing the revascularization procedure of FIG. 1, with different positions of the probe member shown in phantom.

FIG. 3A is an enlarged fragmentary view in section of the device shown in FIG. 2 showing details of the rotatable nose portion of the body including the internal ratchet mechanism.

FIG. 3B is a view similar to FIG. 3A showing the nose portion of the body with a detent wheel of the ratchet mechanism in its retracted position.

FIG. 4 is an exploded fragmentary view showing the detent wheel for the ratchet mechanism with a portion of the body having a fixed ratchet tooth.

FIG. 5A is an end view of the detent wheel taken along line 5A—5A of FIG. 4.

FIG. 5B is an opposite end view of the detent wheel taken along line 5B—5B of FIG. 4.

FIG. 6 is an exploded view in perspective showing the nose-piece and the detent wheel for the device of FIG. 3A.

FIG. 7 is a view in section of the nose piece taken along line 7—7 of FIG. 3A.

FIG. 8 is a fragmentary exploded view in elevation of the probe shaft and its distal end assembly.

FIG. 8A is a fragmentary view in section showing the distal end of FIG. 8 fully assembled.

FIG. 8B is a fragmentary view in section showing a modified distal end assembly.

FIG. 8C is a fragmentary view in section showing a modified distal end assembly without an end liner.

FIG. 8D is a view in section taken along line 8D—8D of FIG. 8.

FIG. 9 is a fragmentary end view of the device showing the control button in a first position after it has completed a TMR procedure involving minimum travel of the fiber bundle and indicating the extension of the optical fiber element from the distal end of the probe.

FIG. 9A is a view in cross section taken along line 9A—9A of FIG. 9.

FIG. 10 is a view similar to FIG. 9 showing the stop member and control button after completing a TMR procedure when set for an intermediate travel distance for the fiber bundle.

FIG. 10A is a view in cross section taken along line 10A—10A of FIG. 10.

FIG. 11 is a view similar to FIG. 9 showing the stop member and control button of the present device after completing a TMR procedure set for maximum travel of the fiber bundle.

FIG. 11A is a view in cross section taken along line 11A—11A of FIG. 11.

DETAILED DESCRIPTION OF PREFERRED EMBODIMENTS

With reference to the drawing, FIG. 1 diagrammatically depicts a human heart 10 with the epicardium 12 of the left ventricle 14 exposed where a Trans-Myocardial Revascularization (TMR) procedure according to the invention is to be performed. Preliminary to the procedure the surgeon makes an incision in the patient's chest to expose the outer wall of the heart's left ventricle. In a human heart the wall of the left ventricle is comprised of an outer layer, the epicardium, the main muscle thickness or myocardium, and the inner layer or endocardium. The epicardium is comprised of a smooth, moist serous membrane which is somewhat tougher than the other tissue layers of the heart muscle.

In carrying out the method of the present invention, the surgeon utilizes a hand-held device 16 which is manipulated to contact the outer surface of the patient's heart in the left ventricle area and form a series of revascularization channels 18 in the myocardium of the heart tissue at selected spaced apart locations. Such channels allow more blood to flow into the heart muscle causing capillary regenesis and ultimate strengthening of the heart muscle.

In accordance with the principles of the invention, each of the channels is formed by first penetrating the epicardium membrane with a tubular piercing element 25 to form a relatively small opening through which at least a portion of the distal end of an optical fiber bundle 26 can thereafter be forced to engage the myocardium. The fiber bundle is connected to a laser energy source 28 at its proximal end. Once through this epicardial opening, a beam of laser energy is emitted in pulses from the distal end of the fiber bundle 26 as it is moved forwardly to form the channel 18 or pocket in the myocardium and in most cases completely through the endocardium. After the channel has been formed, the distal end of the fiber bundle is retracted to a position within the end member of the device 16 which is then moved to another location to repeat the procedure. In a typical TMR operation a number of channels, e.g. up to 60, may be formed depending on the patient's condition. When the end member of the device is removed, the relatively small opening in the epicardium substantially closes due to the tissue resiliency, thereby minimizing any blood flow from the channel just formed.

As shown in FIG. 2, the device 16 comprises a housing body 20 adapted to be hand-held by the surgeon during an operative procedure. A generally J-shaped neck or probe member 22 is attached to a rotatable nose piece 23 attached to the forward end of the housing body 20 so that the probe member 22 can be rotated to different positions as shown in FIG. 2. At the distal end of the probe member is a detachable enlarged head member 24 that surrounds the piercing element 25 and has a disk like shape with a yieldable lining 27 for cushioning contact with the outer surface of the epicardial membrane and for irrigating the TMR site with a solution such as sterile saline or lactated ringers. A portion of the disk may be removed (not shown) to allow visibility of the target site, or the disk may be made from a relatively transparent material. The optical fiber bundle 26 whose proximal end is connected to the laser source 28 extends through the housing and through the neck member to the distal head member 24. Within the housing body 20 the fiber bundle 26 is connected to a movable shuttle 30 (FIGS. 3A and 3B) which is connected to the thumb actuated fiber moving control button 32. Movement of the control button 32 by the surgeon will move the distal end 34 of the fiber bundle forwardly beyond the distal head member 24. As described in greater detail below, means are provided in conjunction with the control button 32 for limiting its travel and thus controlling the extension of the tip of the fiber bundle to a selected distance during each procedure.

A flexible conduit 31 extending from the vacuum source 37, such as a conventional hospital vacuum type canister device, is connected to the vacuum fitting of a conventional stopcock valve 33 that is connected to the rear end of the suction/irrigation hose 36 and communicates with one or more air passages around the fiber bundle that extends to and through the distal head member 24. Also attached to the valve 33 is a conduit 35 connected to an irrigant supply 43. Thus, when in use with vacuum applied, a suction is provided at the distal head member 24 of the device 16 which performs two vital functions. This suction force draws the epicardial tissue firmly against the distal head member 24 so that the piercing element 25 can make a relatively small opening in the epicardial muscle fibers to allow the distal end 34 of the fiber bundle 26 to penetrate and engage the myocardium. The suction further allows additional anchoring of the device to the heart. When irrigant supply is attached to the stopcock valve, rotated to the irrigation position, lactated Ringers or other sterile irrigant from the source 43 is applied to the nose piece section, and through the probe and distal head member 24. The irrigant maintains a moist heart surface during a TMR procedure, and flushes the vacuum/irrigation channel 69 within the body of the device. As the fiber bundle is advanced by the surgeon beyond the epicardial opening and into the myocardium, laser pulses are produced from its distal end 34 to form a channel 18 through the myocardium. With vacuum applied, as the fiber bundle continues to advance, the air suction provided helps to remove debris caused by the laser and also to draw blood into the channel to assure that the revascularization process will commence properly. When the fiber bundle is retracted after forming a channel, the distal head member 24 is moved away and the relatively small pierced opening in the epicardium closes naturally with a minimum of bleeding and with minimal tissue destruction of the epicardium and myocardium directly beneath.

Describing now the device 16 in greater detail, with reference to FIGS. 2, 3A and 3B, the housing body 20, may be comprised of assembled components molded from a suitable plastic material. In general, it comprises a central portion 38 that houses the shuttle 30 and the control button 32. A molded rubber rear end portion 39 extends at an angle from the control portion and provides strain relieved access holes for the suction/irrigation hose 36 and the fiber bundle 26. At the forward end of the body 20 is the rotatable nose piece 23 which enables the attached J-shaped probe 22 and its distal head member 24 to be turned up to 360° in a desired direction. The exterior of the central member 38 is provided with elongated recesses 40 on opposite sides to enable it to be gripped firmly, and the nose piece is provided with similar slight depressions 41 on opposite sides of an outwardly extending control fin 42.

As shown in FIG. 3A, the internal shuttle 30 is bonded to the fiber bundle 26 and is connected by a web position 44 to the control button 32 which extends through and is movable within a slot 45 (FIG. 2) in the body wall. Below the shuttle, a tubular plastic conduit 46 is attached to an internal barb 47 forming a suction/irrigation passage 48 that extends through the nose piece 23 and the probe member to its distal head member 24. The nose piece, which is tapered forwardly, is combined with other interior components to form a ratchet means that enables it and thus the probe member 22 to be rotatively indexed in increments and to stay in a selected position when rotated by the surgeon. As shown in FIG. 3A, the tubular probe member 22 extends through and is bonded to a series of cruciform internal fins 56 at the forward end of the nose-piece 23. One of the cruciform fins 56 has a spline member 57 as shown in FIG. 7 which engages into a slotted opening in the tubular probe member 22. The spline maintains correct orientation of the J-shaped probe to the nose-piece during assembly, and reinforces the adhesive bond against rotational force during use. Within the nose-piece, the end of the probe member extends within and is bonded to the surface of a central bore 49 of a detent wheel 50. As shown in FIG. 5A this detent wheel has an enlarged flange portion 51 having a series of blunt cogs or teeth 52 separated by spaces 53. Extending forwardly from the flange portion is an integral tubular portion 54, which fits around and slides over the outer surface of the inner end of the probe member 22. The end of tubular portion 54 is provided with cruciform slots 55 that mesh with cruciform internal fins 56 within the end of the nose-piece 23. (See FIG. 6) Spaced outside of and coaxial with the detent wheel 50 is a tubular sleeve 58 having radially outwardly extending end flange 59. The forward end of this sleeve bears against the cruciform fins of the nose-piece 23 and in this position, the end flange 59 retains an O-ring 60 between it and an end flange 61 of the central body member 38. The O-ring 60 maintains a compression fit between the nose-piece and the control body while allowing ready rotation of the nose-piece.

Situated around the tubular portion 54 of the detent wheel 50 in the annular space between it and the sleeve 58 is a coiled spring 62 which normally urges the end flange 51 of the detent wheel 50 away from the sleeve flange 59. When in this position, as shown in FIG. 3A, a fixed tooth 64 on the inner wall of the central body member 38 as shown in FIGS. 4 and 6 is retained in one of the spaces 53 between two teeth 52, thereby holding the nose-piece 23 and the attached probe member 22 in a fixed position. Now, if the surgeon wishes to change the orientation of the probe member 22 and its distal head end 24, side pressure is applied to the nose fin 42. As this is done the fixed tooth 64 or the body interior bears against a tapered tooth 52 of the detent wheel 50 and creates a camming action that moves the detent wheel axially against the spring 62. This allows the nose-piece 23 and the detent wheel 50 to rotate until pressure on the fin 42 is released, allowing the detent wheel 50 to move axially so that the fixed tooth 64 becomes seated in another space between teeth 52 of the detent wheel. This relatively simple mechanical ratchet system enables the device user to rotate the probe element 22 and its distal end 24 to any desired position with a positive action that produces a responsive ratchet click which indicates that with no pressure on the fin, the nose-piece and probe member will remain in the desired set position.

To prevent any tendency for the fiber bundle to bend or buckle within the body 20 as it is being advanced during normal operation of the device, a supporting tube 65 is provided within the body and its nose-piece 23. As shown in FIG. 3A, with the fiber moving control button pushed fully distally, this tube extends from the shuttle 30 forwardly and somewhat beyond the forward end of the nose-piece. It is made of semi-rigid material and fits around the fiber bundle 26, being sized to provide an easy sliding clearance within the probe member 22. It is co-axial with the probe member 22 which has a larger diameter so that an annular suction/irrigation passage 48 is provided around it.

The enlarged distal head member 24 on the J-shaped probe member 22 as shown in FIG. 8 and 8A, provides a means for quick attachment and replacement of optional distal head members whenever it is necessary.

The device 16 according to the present invention may utilize different distal head member configurations as shown in FIGS. 8–8C. For example, as shown in FIGS. 8 and 8A a distal head member 24 is provided having a piercing tip 25, a foam lining 27 and suction/irrigation passages 69. In FIG. 8B a distal head 24A is shown without a piercing tip and without an irrigation lining. In FIG. 8C, a distal head embodiment 24C is shown which has a tip member 25C but no irrigation liner. Other combinations are included within the scope of the invention. All of the distal head members utilize Luer style fittings to enable quick attachment and removal. To secure the optional distal head members to the probe member 22, a standard male Luer connector sleeve 66 is bonded to the distal end of the probe member. Each of the distal head members includes a tubular female Luer fitting 68 which receives the male Luer connector sleeve 66. A Luer retaining nut 74 is moved into place and twisted onto the Luer threads of the tubular female Luer fitting and twisted to hold the distal head member assembly to the probe member assembly. The piercing suction irrigation tip is comprised of a tubular female Luer into which is bonded the piercing tip 25. The tubular holder 67 has a large bore 68 at one end to receive the male Luer connecting sleeve 66, and the tubular piercing tip 25 extends from its lower end. As shown in FIGS. 8 and 8C, a series of channels 69 which are generally parallel to the axis of the tip holder extend from the bore 68 to its lower end 70 which is within the concave cup area of the head member 24A, thereby communicating the suction or irrigation to the area where the epicardium is penetrated during a TMR procedure. The piercing tip 25, preferably made of 304 Hypodermic stainless steel is tubular with its outer, or lower end beveled at something less than 60°. The inside edge of the piercing tip is slightly radiused, and the distal tip is flared approximately 0.005" to allow fiber movement without restriction. The proximal end of the piercing tip 25 is slightly flared to mechanically prevent the tip from falling out of the tubular female Luer fitting 67, and is also bonded to the fitting. The piercing tip head member 24A further includes a conical disk member 71 with a central opening 72 which receives the lower end 70 of the female Luer fitting 67 and is surrounded by a smooth inner concave surface 73. The irrigation tip head member is identical to a plain suction/irrigation tip with the additional layer 27 of medical grade, plastic foam material bonded to the conical disc member. This foam layer has a central opening and preferably extends outwardly from the cup member to provide a means for cushioning the contact of the head member 24A with the heart surface. It also provides a means for applying a liquid solution such as irrigants and/or drugs to the heart surface when necessary during the TMR procedure.

When the distal head 24 is assembled for use as shown in FIG. 8A, the tip holder 67 is retained by the lower end portion 70 which extends through the central opening 72 of the disk member. The piercing tip 25 extends through the opening in the plastic foam liner material 27 on the inner concave surface of disk member. Now, the tip holder 67 is pushed into the Luer sleeve connector 66 on the J-shaped probe member 22 and a Luer retainer nut 74 is moved into place and twisted to hold the assembly together. As shown, when assembled the beveled end of the piercing tip 25 extends just slightly beyond the outer surface of the foam layer 27.

Referring now to FIGS. 9–11, as stated previously, the device 16 is provided with a means for controlling the amount or distance of travel for the control button 32 and thus the distance that the distal tip 34 of the fiber bundle 26 will move from the distal head 24 of the J-shaped probe member 22 during a typical TMR procedure. Before each procedure cycle commences, the control button 32 on the body 20 is in its rearward or starting position, that is, at the rear of the slot 45 in the body. Spaced from the rear end of the slot and to the right side of it is a first projection or stop member 76 that is integral with the body and extends outwardly therefrom. Further forward of stop member 76 and to the left side of the slot 45 on the body 20 is a second projection or stop member 78. The projections 76 and 78 serve as stops to limit the travel of the control button 32 to two preset travel distances. As shown in FIGS. 9 and 9A an arcuate member 80 having a curvature that conforms to the outer cylindrical surface of the upper side of the body 20, extends through the control button 32 on a line that is transverse to its direction of movement, i.e. the longitudinal axis of the body 20. At the ends of the arcuate member 80 are upwardly extending projections 81 and 82. The arcuate member 80 defines a slot 83 which locally decreases stiffness to create a leaf spring with fixed ends. The arcuate member 80 defines in the leaf spring area a small projection 87 which fits within a mating recess 89 in the button when the arcuate member 80 is centered as shown in FIG. 11. When the arcuate member 80 is slid from side to side, as shown in FIGS. 9 and 10 and as described below, the projection 87 moves out of the recess and deflects the leaf spring until the member is returned to the centered position. The force created by the deflection creates frictional drag and resistance to positional change of the arcuate member.

When the arcuate member 80 is pushed to one side, e.g. the right side in FIGS. 9 and 9A, the left end projection 82 engages the left wall of the control button and the right end projection 81 extends outwardly to be in line with the first stop member 76. Thus, as shown in FIG. 9, with the arcuate member pushed to the right, the control button 32 can be moved only a preselected distance (e.g. 2.5 centimeters) until the right end projection 81 engages the first stop member 76. This allows the distal tip 34 of the fiber bundle 26 to move the same preselected distance from the surface of the distal end assembly 24 of the probe member 22.

In FIGS. 10 and 10A, the arcuate member 80 is shown when pushed to the left so that its left end projection 82 will engage the second stop member 78. This position of the arcuate member limits the travel of the control button and thus the tip 34 of the fiber bundle 26 to a selected intermediate distance, e.g. (3 centimeters). When the arcuate member 80 is centered on the control button 32, as shown in FIGS. 11 and 11A the control button can be moved its full travel distance which is limited only by the length of the slot 45. Thus, it is seen from FIGS. 9–11 that with the device 16, the operating surgeon can accommodate varying patient characteristics and conditions by preselecting the length of travel of the fiber bundle tip as it moves through the myocardium.

The function of the device 16 in a typical TMR operation should be readily apparent from the foregoing description. In summary, for each TMR procedure the device is gripped and maneuvered by the surgeon, using the rotatable nosepiece 23 and attached probe member controlled by the nose fin, so that the distal head member of the probe can engage the desired target area of the patient's beating heart. As described above, the ratchet system allows firm positioning of the probe member at any selected position by applying side pressure to the nose-piece fin member. Once the heart has been engaged, if used, vacuum force through the device will cause the epicardial layer of the heart to conform firmly to concave disk of the head member 24. At this point the epicardium is mechanically pierced by the piercing tip 25. Almost immediately, the surgeon can move the distal tip 34 of the optical fiber bundle forwardly by pushing the control button 32. Simultaneously, the surgeon can activate the laser source with an appropriate switch such as a foot switch (not shown), thereby causing laser pulses to be emitted from the distal tip 34 as it moves forward. Prior to the procedure, the surgeon can preset the amount of travel of the distal tip by moving the arcuate member 80 on the control button to either or none of the stop members 76 and 78.

The proximal end of the optical fiber bundle 26 is connected to the source or generator 28 of laser energy which is preferably a Holmium laser that operates at a wave length in the range of 1.8 to 2.2 microns and a pulse frequency in the range of 2–25 Hertz. A Holmium or Excimer laser is preferable because it provides high absorption efficiency, hemotosis and a moderate absorption range in myocardium tissue, and is compatible with optical fiber delivery. At the laser generator, laser energy is supplied to the optical fiber bundle 26 which, at its distal end, has a diameter of less than 1.5 mm and sized according to the location and type of laser(s) to be used. The optical fiber bundle preferably is comprised of a plurality (e.g. 37) of glass fibers 32 each having a diameter of 100 microns. These glass fibers are held together by a suitable bonding or potting material, such a 353 ND Epoxy, and near its distal tip, the bundle is preferably surrounded by an annular tantalum marker which serves to retain the bundle in a closely packed geometric boundary. Surrounding the bundled fibers is a plastic protective sheath such as polypropelene having a wall thickness of 0.004 inches. Other fiber bundle configurations or a single fiber could be used within the scope of the invention.

In the embodiment shown, the probe member 22 of the device 16 is a tubular member preferably made from stainless steel and having a uniform outside diameter (e.g. 0.120 inches), an inside diameter (e.g. 0.094 inches) and bent into an angular "J" shape within which the optical fiber bundle 26 is slidable.

From the forgoing it is apparent that the present invention provides an improved laser surgery device for performing TMR procedures that is particularly easy to manipulate and maneuver during use and has adjustment features which increase its versatility and efficiency in the formation of effective channels for revascularization.

To those skilled in the art to which this invention relates, many changes in construction and widely differing embodiments and applications of the invention will make themselves known without departing from the spirit and scope of the invention. For instance, various types of tips may be attached to the probe. Also, the fiber may be a single fiber or other fiber bundle arrangements may be used, and the laser energy may be provided by other lasers. Additionally, the stop mechanism may include more or less stops and other conventional means may be used for controlling the distance of travel of the fiber. The disclosure and the description herein are purely illustrative and are not intended to be in any sense limiting.

What is claimed is:

1. A hand-held device for use in performing transmyocardial revascularization comprising:
    a housing having a ratcheting means therein and a distal rotatable nose piece, the nose piece attached to the ratcheting means;
    a probe member having proximal and distal ends, the proximal end attached to the housing and operatively connected to the rotatable nose piece, the ratcheting means thereby enabling incremental rotation of the nose piece to selected positions to change orientation of the probe member;
    a head member having a connector attached to the distal end of the probe member;
    at least one optical fiber having proximal and distal ends, the proximal end adapted for attachment to a source of laser energy, the optical fiber extending through the housing, the probe member and the head member; and
    an adjustment mechanism on the housing and connected to the optical fiber for moving the optical fiber.

2. The hand-held device of claim 1 wherein the head member further includes a generally disc shaped tip attached to the connector, the disc shaped tip forming a tissue contact surface.

3. The hand-held device of claim 2 wherein at least a selected portion of the disc shaped tip is removed to enable visualization of tissue.

4. The hand-held device of claim 2 wherein at least a portion of the disc shaped tip is transparent to enable visualization of tissue.

5. The hand-held device of claim 2 wherein the head rnember further comprises a tubular piercing member extending therefrom to enable epicardial piercing and anchoring of the head member during a transmyocardial revascularization procedure.

6. The hand-held device of claim 5 further comprising a cushioning member attached to the disc shaped tip and surrounding the tubular piercing member, the cushioning member compressible to enable the tubular piercing member to pierce tissue.

7. The hand-held device of claim 6 wherein the cushioning member comprises a medical-grade plastic foam capable of absorbing fluids.

8. The hand-held device of claim 2 further comprising a cushioning member attached to the disc shaped tip thereby providing a yieldable tissue contact surface.

9. The hand-held device of claim 8 wherein the cushioning member comprises a inedical-grade plastic foam capable of absorbing fluids.

10. The hand-held device of claim 1 wherein the ratcheting means comprises a detent member having a generally circular flange comprising teeth separated by spaces, a projection attached within the housing, and a spring means for urging the detent member against the projection so that the projection seats in one space while allowing the detent member to retract and the projection to seat in another space when rotating the nose piece.

11. The hand-held device of claim 1 wherein the nose piece has an outwardly extending projection thereby enabling rotational ease of the nose piece.

12. The hand-held device of claim 1 wherein the housing includes a slot and the adjustment mechanism comprises: a movable control button mounted within the slot, a shuttle within the housing and attached to the at least one optical fiber, and a web mechanism extending through the slot for connecting the shuttle to the control button such that movement of the control button within the slot moves the distal end of the at least one optical fiber into and out of the head member.

13. The hand-held device of claim 12 wherein the housing includes a stop assembly for limiting movement of the control button within the slot thereby controlling displacement of the at least one optical fiber out of the head member.

14. The hand-held device of claim 12 wherein the stop assembly, the control button and the rotatable nose piece are positioned on the housing to enable a user single-handed motion control of both the at least one optical fiber and the rotatable nose piece to change orientation of the probe member.

15. The hand-held device of claim 12 wherein the stop assembly comprises projections extending outwardly from the housing and a cross member attached to the control button and having mating projections, the cross member slidable within the control button to select a travel distance for the control button prior to engagement of a housing projection by a mating projection of the cross member.

16. The hand-held device of claim 15 wherein the cross member has a central position within the control button, the central position enabling the control button unrestricted movement within the slot without engagement of the projections of the housing with the cross member mating projections, the cross member further having left and right positions within the control button, movement of the control button with the cross member in the left position limiting travel of the control button to a first preselected distance when a first projection of the housing engages a cross member projection, the right position limiting travel of the control button to a second preselected distance when a second projection of the housing engages an opposite cross member projection.

17. The hand-held device of claim 1 further comprising a tubular support member within at least the distal rotatable nose piece and surrounding at least the distal end of the at least one optical fiber.

18. The hand-held device of claim 1 wherein the connector is a Luer taper and lock mechanism for providing quick interchangeability of the head member.

19. The hand-held device of claim 1 further comprising at least one fluid passage extending through the housing, the probe member and the head member, the at least one fluid passage having a proximal end adapted for connection to a fluid source and a vacuum source.

20. The hand-held device of claim 19 wherein the proximal end of the fluid passage is attached to a fitting enabling selection of an irrigation mode to allow passage of fluid from the fluid source to the head member and selection of a suction mode.

21. The hand-held device of claim 1 wherein the at least one optical fiber is a bundle of fibers.

22. The hand-held device of claim 1 wherein the at least one optical fiber is a single fiber.

23. A surgical hand piece for use in performing laser transmyocardial revascularization comprising:
    a housing having proximal and distal ends, the distal end having a rotatable nose piece;
    a tubular probe member having proximal and distal ends, the proximal end attached to the distal end of the housing and the distal end of the tubular probe member extending outwardly through the rotatable nose piece, the tubular probe member connected to and rotatable by the rotatable nose piece;

a head member having a connector and a distal tip, the connector attached to the distal end of the tubular probe member, the distal tip forming a disc with a tissue contacting surface;

at least one fluid passage extending through the housing, the nose piece, the probe member and the head member, the fluid passage adapted for connection to a fluid source at the proximal end of the housing;

at least one optical fiber having proximal and distal ends, the proximal end adapted for connection to a source of laser energy, the distal end extending through the housing, the nose piece, the probe member and the bead member; and an adjustment mechanism disposed on the housing for moving the at least one optical fiber.

24. A surgical device for performing transmyocardial revascularization on a patient's heart comprising:

a body portion having a ratchet means therein and a rotatable nose piece attached to the ratchet means, the ratchet means for enabling the nose piece to be rotated in increments and to be retained in any selected position;

a tubular probe member connected to the body portion and rotatable by the nose piece on the body portion, the probe member defining proximal and distal ends; a head assembly attached to the distal end of the probe member and including a quick disconnect connector adapted for attaching thereto a tip member;

an optical fiber means having a proximal end adapted for connection to a source of laser energy, the fiber means extending through the body portion and into the probe member, the fiber means having a distal end extending through the head assembly; and control means on the body portion for moving the fiber means axially therein thereby moving the distal end of the fiber means forwardly from the head assembly to emit laser pulses when connected to the source to form revascularization channels in a myocardial layer of the heart.

* * * * *